United States Patent [19]

Shiraki et al.

[11] Patent Number: 5,260,500
[45] Date of Patent: Nov. 9, 1993

[54] PRODUCTION OF LINEAR α-OLEFIN

[75] Inventors: Yasushi Shiraki; Takao Tamura, both of Tokuyama, Japan

[73] Assignee: Idemitsu Petrochemical Co., Ltd., Tokyo, Japan

[21] Appl. No.: 770,626

[22] Filed: Oct. 3, 1991

[30] Foreign Application Priority Data

Oct. 19, 1990 [JP] Japan ................. 2-279203

[51] Int. Cl.$^5$ ............................. C07C 2/02
[52] U.S. Cl. ..................... 585/524; 585/520; 585/521; 585/522; 585/523
[58] Field of Search ............ 585/520, 521, 522, 523, 585/524

[56]         References Cited
         U.S. PATENT DOCUMENTS

| 3,474,157 | 10/1969 | White et al. | 585/524 |
|---|---|---|---|
| 3,725,497 | 4/1973 | Arakawa et al. | 585/524 |
| 3,737,476 | 6/1973 | Bailly | 585/524 |
| 4,396,788 | 8/1983 | Langer, Jr. | |
| 4,579,991 | 4/1986 | White | 585/524 |
| 4,590,325 | 5/1986 | Imai et al. | 585/524 |
| 4,642,410 | 2/1987 | Loveless | 585/522 |

FOREIGN PATENT DOCUMENTS

| 0241596 | 10/1987 | European Pat. Off. |
|---|---|---|
| 0295960 | 12/1988 | European Pat. Off. |
| 0320571 | 6/1989 | European Pat. Off. |
| 0328728 | 8/1989 | European Pat. Off. |
| 0358763 | 3/1990 | European Pat. Off. |

OTHER PUBLICATIONS

Chemical Abstracts, vol. 88, No. 2, p. 20, Jan. 9, 1978, Columbus, Ohio, US; Abstract No. 7666x of Furhrmann et al, DD 125 623 (1977).

*Primary Examiner*—Patrick P. Garvin
*Assistant Examiner*—E. D. Irzinski
*Attorney, Agent, or Firm*—Frishauf, Holtz, Goodman & Woodward

[57] ABSTRACT

Disclosed herein is a process for producing a linear α-olefin by the oligomerization of ethylene, characterized in that the oligomerization is carried out in the presence of a catalyst composed of (A) titanium halide or zirconium halide, (B) an organoaluminum compound, and (C) an alcohol (methanol and/or ethanol). The linear α-olefin has an extremely high purity because it is not contaminated with the catalyst components.

17 Claims, No Drawings

PRODUCTION OF LINEAR α-OLEFIN

BACKGROUND OF THE INVENTION

1. Field of the Invention:

The present invention relates to a process for producing a linear α-olefin, more particularly, to a process for producing a high-purity linear α-olefin.

2. Description of the Prior

A linear α-olefin is useful as a comonomer for modification of polyolefins or as a raw material for plasticizers and surface active agent. In particular, a linear α-olefin having 6 to 18 carbon atoms is used in general.

A linear α-olefin of this type is conventionally produced by the oligomerization of ethylene which is accomplished by the aid of a catalyst composed of titanium or zirconium halide and an organoaluminum compound.

It is known that, in a process for producing a linear α-olefin, it is effective to add to the catalyst a sulfur compound, phosphorus compound, or nitrogen compound as a third component, in order to improve the purity of the linear a-olefin. A particularly effective sulfur compound includes dimethyl disulfide, thiophene, and thiourea. However, there is a disadvantage of contaminating a part of said third component into the linear α-olefin, when the catalyst being incorporated with said third component is used.

In order to eliminate this disadvantage, the present inventors carried out serious research on the process for producing a high-purity α-olefin free of contaminant. As the result, it was found that a sufficient effect can be obtained by the use of a small amount of a specific alcohol in place of the sulfur compound as a third component. This finding led to the present invention.

SUMMARY OF THE INVENTION

It is an object of the present invention to provide a process for producing a linear α-olefin by the oligomerization of ethylene, characterized in that the oligomerization is carried out in the presence of a catalyst composed of (A) titanium halide or zirconium halide, (B) an organoaluminum compound, and (C) an alcohol.

DETAILED DESCRIPTION OF THE INVENTION

According to the present invention, the catalyst used in the process is composed of the following three components.

Component (A): titanium halide or zirconium halide
Component (B): an organoaluminum compound
Component (C): an alcohol The titanium halide or zirconium halide as component (A) is represented by the formula [I] below.

$$MX_aA_{4-a} \quad [I]$$

(where M denotes a titanium or zirconium atom; each of X and A denotes a chlorine atom, bromine atom, or iodine atom wherein X and A may be the same or different each other; and a denotes zero or an integer of 1 to 4).

There are no restrictions on component (A) so long as it is a compound which satisfies the formula [I]. Typical examples of the compound include $ZrCl_4$, $ZrBr_4$, $ZrI_4$, $ZrBrCl_3$, $ZrBr_2Cl_2$, $TiCl_4$, $TiBr_4$, $TiI_4$, $TiBrCl_3$, $TiBr_2Cl_2$, etc. Among these compounds, zirconium halide is preferable, and $ZrCl_4$ is particularly preferable.

The titanium halides and zirconium halides represented by the formula [I] may be used alone or in combination with one another or more.

The organoaluminum compound as component (B) is a compound represented by the formula [II] below or a compound represented by the formula [III] below.

$$AlR_cQ_d \quad [II]$$

(where R denotes an alkyl group having 1 to 20 carbon atoms; Q denotes a chlorine atom, bromine atom, or iodine atom; c and d are numbers selected from 1, 1.5, and 2, with c+d=3.)

$$AlR'_3 \quad [III]$$

(where R' denotes an alkyl group having 1 to 20 carbon atoms.)

Examples of the compound represented by the formula [II] include $Al(C_2H_5)Cl_2$, $Al(C_2H_5)Br_2$, and $Al(C_2H_5)I_2$ (in case of c=1 and d=2); and $Al(CH_3)_{1.5}Cl_{1.5}$, $Al(CH_3)_{1.5}Br_{1.5}$, $Al(C_2H_5)_{1.5}Cl_{1.5}$, $Al(C_2H_5)_{1.5}Br_{1.5}$, $Al(C_2H_5)_{1.5}I_{1.5}$, $Al(C_3H_7)_{1.5}Cl_{1.5}$, $Al(iso-C_3H_7)_{1.5}Cl_{1.5}$, $Al(C_4H_9)_{1.5}Cl_{1.5}$, $Al(iso-C_4H_9)_{1.5}Cl_{1.5}$, $Al(C_6H_{13})_{1.5}Cl_{1.5}$, $Al(C_2H_5)_{1.5}Br_{0.5}Cl$, $Al(C_8H_{17})_{1.5}Cl_{1.5}$, and $Al(C_2H_5)(CH_3)_{0.5}Cl_{1.5}$ (in case of c=1.5 and d=1.5). Preferable of these examples are those in which R is a methyl, ethyl, propyl, or butyl group. The one in which R is an ethyl group is most desirable. Also, preferable of these examples are those in which Q is a chlorine atom. In the case where c=2 and d=1, $Al(C_2H_5)_2Cl$, $Al(C_2H_5)_2Br$, and $Al(C_2H_5)_2I$ are preferable. The compounds represented by the formula [II] may be used alone or in combination with one another or more.

Examples of the compound represented by the formula [III] include $Al(CH_3)_3$, $Al(C_2H_5)_3$, $Al(C_3H_7)_3$, $Al(iso-C_3H_7)_3$, $Al(C_4H_9)_3$, $Al(iso-C_4H_9)_3$, $Al(C_5H_{11})_3$, $Al(C_6H_{13})_3$, and $Al(C_8H_{17})_3$. Among these compounds, preferable compounds are those in which R' is a methyl, ethyl, propyl, or butyl group. The compounds represented by the formula [III] may be used alone or in combination with one another or more.

In addition, the organoaluminum compound as component (B) may be a combination of compounds represented by formulas [II] and [III].

Preparation of the above-mentioned catalyst components are performed by using an inert solvent, which includes aromatic hydrocarbons with or without substituting halogen atom(s) (such as benzene, toluene, xylene, chlorobenzene, ethylbenzene, dichlorobenzene, and chlorotoluene); aliphatic hydrocarbons (such as pentane, hexane, heptane, octane, nonane, and decane); alicyclic hydrocarbons (such as cyclohexane); naphthenic paraffins (such as decalin); and haloalkanes (such as dichloroethane and dichlorobutane).

According to the present invention, the catalyst components (A) and (B) are used in such amounts that the Al/Zr (or Al/Ti) molar ratio is in the range from 1 to 15. The compounds [II] and [III] for component (B) are used in such amounts that the molar ratio of compound [II] to compound [III] is in the range from 2 to 10.

According to the present invention, the above-mentioned catalyst components are combined with component (C), which is an alcohol, for the oligomerization of ethylene. Examples of the alcohol include methanol, ethanol, and propanol. It is desirable to use methanol and ethanol singly or in combination with each other.

The alcohol may be added when the catalyst is prepared or added directly to the reaction system. The alcohol should be added in an amount 0.1–6 times (in mol) the amount of component (A), with methanol being 0.1–5 times, preferably 0.3–2.0 times, and ethanol being 0.1–3 times, preferably 0.1–1 time.

The alcohol contributes to the improvement of product purity ($\alpha$-olefin content) and activity without any adverse effect on the catalytic activity.

The oligomerization of ethylene is usually carried out at a temperature in the range from 100° C. to 150° C. under a pressure higher than 25 kg/cm$^2$G. The reaction time usually ranges from 15 minutes to 1 hour, depending on the reaction temperature and pressure.

The unreacted ethylene dissolved in the reaction product is removed therefrom by the method of adiabatic flashing and then the reaction product is subjected to a deactivation treatment of catalyst. The linear $\alpha$-olefin is separated from the solvent by distillation. The recovered ethylene and solvent are recycled to the reaction system.

The alcohol added is easily separated together with deactivating agent such as water, from the reaction product at the time of catalyst deactivation.

The linear $\alpha$-olefin of the present invention is obtained in the form of a mixture of linear $\alpha$-olefins having 4 or more carbon atoms as the result of ethylene oligomerization. The mixture can be separated into fractions by multistage distillation. In addition, it is possible to obtain selectively a linear $\alpha$-olefin having a desired number of carbon atoms by appropriately selecting and controlling the reaction conditions.

In the process of the present invention an alcohol is used as the third component in place of sulfur compounds, phosphorus compounds and nitrogen compounds which are used in the conventional process. The alcohol does not contaminate into the desired product, and also it is easily separated from the desired product when the catalyst is deactivated. Thus, with the process of the present invention, it is possible to produce a linear $\alpha$-olefin of high purity.

According to the present invention, a process which employs a catalyst incorporated with an alcohol as a third component is provided. In the process of the present invention, the catalyst components are prevented from contaminating into the product and the purity of the product can be improved. Therefore, with the process of the present invention, it is possible to produce effectively a linear $\alpha$-olefin of extremely high purity. The linear $\alpha$-olefin is useful as a comonomer for modification of polyolefins and also as a raw material for plasticizers and surface active agents.

The invention will be described in more detail with reference to the following examples, which are not intended to restrict the scope of the invention.

EXAMPLE 1

(1) Preparation of catalyst

In a 500-ml flask equipped with a stirrer were introduced 25 mmol of anhydrous zirconium tetrachloride and 250 ml of dried cyclohexane under an atmosphere of argon. After stirring for 10 minutes, triethyl aluminum (($C_2H_5$)$_3$Al) and ethyl aluminum sesquichloride (($C_2H_5$)$_3$Al$_2$Cl$_3$) were added one after the other. The amounts of triethyl aluminum and ethyl aluminum sesquichloride were established such that ($C_2H_5$)$_3$Al$_2$Cl$_3$/($C_2H_5$)$_3$Al=3.5 (in molar ratio) and {($C_2H_5$)$_3$Al+($C_2H_5$)$_3$Al$_2$Cl$_3$}/ZrCl$_4$=7 (in molar ratio).

The reactants were heated with stirring at 70° C. for 2 hours under an atmosphere of argon to form a complex. Thus there was obtained a catalyst solution. Alcohol was added to the reaction system.

(2) Production of linear $\alpha$-olefin

In a 1-liter autoclave equipped with a stirrer, which had been dried under an atmosphere of argon, was introduced 260 ml of dried cyclohexane. Into the autoclave was introduced dried ethylene gas until the pressure reached 30 kg/cm$^2$G. The autoclave was heated to 120° C. During heating, methanol was added in an amount of 0.025 mmol, which is half the amount (in mol) of zirconium tetrachloride. The autoclave at 120° C. was supplied with the catalyst solution (containing 0.05 mmol of zirconium tetrachloride) from the catalyst pot attached to the autoclave and then with ethylene gas rapidly until the pressure in the autoclave reached 65 kg/cm$^2$G.

The contents in the autoclave were stirred to start oligomerization reaction. The reaction product was sampled (about 5 cc each) at a predetermined time intervals for analysis by gas chromatography. During the reaction, the above-mentioned pressure was kept by continuously supplying ethylene. Sampling was carried out by receiving the reaction product in a water-containing cooled bottle so that the catalyst is deactivated and the reaction product is not affected by the catalyst after sampling.

The sample of the reaction product was mixed with 1 g of undecane as the internal standard substance for gas chromatography. The resulting solution was freed of water and then dried with anhydrous potassium carbonate. The thus dried sample was used for analysis. The yields of $C_4$–$C_6$ fractions were estimated from the Schulz-Flory distribution because they are inevitably lost to some extent in handling the sample. The results are shown in Table 1.

EXAMPLE 2

The same procedure as in Example 1 was repeated, except that the amount of methanol was changed to 0.05 mmol, which is equal to the amount (in mol) of zirconium tetrachloride. The results are shown in Table 1.

EXAMPLE 3

The same procedure as in Example 1 was repeated, except that methanol was replaced by ethanol. The results are shown in Table 1.

EXAMPLE 4

The same procedure as in Example 3 was repeated, except that the amount ethanol was changed to 0.05 mmol, which is equal to the amount (in mol) of zirconium tetrachloride. The results are shown in Table 1.

COMPARATIVE EXAMPLE 1

The same procedure as in Example 1 was repeated, except that alcohol was not added. The results are shown in Table 1.

EXAMPLE 5

The same procedure as in Example 1 was repeated, except that the amounts of triethyl aluminum and ethyl aluminum sesquichloride were established such that ($C_2H_5$)$_3$Al$_2$Cl$_3$/($C_2H_5$)$_3$Al=2 (in molar ratio) and $\{(C_2H_5)_3Al+(C_2H_5)_3Al_2Cl_3\}/ZrCl_4=5$ (in molar ratio). The results are shown in Table 1.

EXAMPLE 6

The same procedure as in Example 5 was repeated, except that methanol was replaced by ethanol. The results are shown in Table 1.

EXAMPLE 7

The same procedure as in Example 5 was repeated, except that methanol was replaced by isopropanol. The results are shown in Table 1.

COMPARATIVE EXAMPLE 2

The same procedure as in Example 5 was repeated, except that alcohol was not added. The results are shown in Table 1.

No alcohol was detected in all the samples taken from the reaction products in the above Examples and Comparative Examples.

TABLE 1

| | Example 1 | Example 2 | Example 3 | Example 4 | Compar. Example 1 | Example 5 | Example 6 | Example 7 | Compar. Example 2 |
|---|---|---|---|---|---|---|---|---|---|
| Catalyst components | | | | | | | | | |
| $ZrCl_4$ (mmol) | 0.05 | 0.05 | 0.05 | 0.05 | 0.05 | 0.05 | 0.05 | 0.05 | 0.05 |
| EASC (*1) (mmol) | 0.272 | 0.272 | 0.272 | 0.272 | 0.272 | 0.167 | 0.167 | 0.167 | 0.167 |
| TEA (*2) (mmol) | 0.078 | 0.078 | 0.078 | 0.078 | 0.078 | 0.083 | 0.083 | 0.083 | 0.083 |
| Al/Zr (*3) (molar ratio) | 7 | 7 | 7 | 7 | 7 | 5 | 5 | 5 | 5 |
| EASC/TEA (molar ratio) | 3.5 | 3.5 | 3.5 | 3.5 | 3.5 | 2 | 2 | 2 | 2 |
| Alcohol | methanol | methanol | ethanol | ethanol | — | methanol | ethanol | isopropanol | — |
| Amount of alcohol (mmol) | 0.025 | 0.05 | 0.025 | 0.05 | — | 0.025 | 0.025 | 0.025 | — |
| Activity and (purity)* | | | | | | | | | |
| Reaction time. 10 min | 2750 (97.5) | 2680 (97.6) | 2450 (97.3) | 2200 (97.8) | 2690 (97.1) | 4030 | 3300 | 2950 | 3930 |
| Reaction time. 20 min | 5560 (96.5) | 5460 (96.3) | 4950 (96.3) | 4380 (95.6) | 5450 (95.3) | 7720 | 6730 | 5030 | 7830 |
| Reaction time. 30 min | 8400 (94.5) | 8420 (94.5) | 7350 (95.3) | 6510 (95.2) | 8180 (92.8) | 11800 (94.5) | 10280 (94.7) | 8560 (93.3) | 11700 (92.0) |
| Reaction time. 40 min | 10900 (92.8) | 10850 (93.0) | 9850 (93.6) | 8700 (93.5) | 11100 (89.3) | 15500 | 13500 | 10800 | 15800 |
| Reaction time. 50 min | 13750 (90.3) | 13700 (90.9) | 12400 (91.3) | 10320 (91.5) | 13650 (86.9) | 18800 | 17100 | 14100 | 18500 |
| $C_4$ fraction (wt %) | 15.1 | 15.4 | 16.8 | 16.9 | 15.5 | 7.8 | 7.9 | 8.9 | 8.6 |
| $C_6$ fraction (wt %) | 15.5 | 16.5 | 16.8 | 16.8 | 15.8 | 9.2 | 9.3 | 10.3 | 9.6 |
| $C_8$ fraction (wt %) | 14.2 | 14.7 | 14.9 | 14.9 | 14.3 | 9.5 | 9.7 | 10.5 | 10.2 |
| $C_{10}-C_{18}$ fraction (wt %) | 41.1 | 40.3 | 40.2 | 40.0 | 40.9 | 39.5 | 39.6 | 40.8 | 40.4 |
| $C_{20}-$ fraction (wt %) | 14.1 | 12.1 | 11.3 | 11.4 | 13.5 | 34.0 | 33.5 | 29.5 | 30.9 |

*1 $(C_2H_5)_3Al_2Cl_3$
*2 $(C_2H_5)_3Al$
*3 $\{(C_2H_5)_3Al + (C_2H_5)_3Al_2Cl_3\}/ZrCl_4$
Activity is expressed in terms of g/g-Zr.
Purity is expressed in terms of the concentration (wt %) of 1-octadecene in the $C_{18}$ fraction.

What is claimed is:

1. A process for producing a liquid linear α-olefin comprising oligomerizing ethylene in the presence of a catalyst comprising
   (A) a zirconium halide,
   (B) an organoaluminum compound comprising a combination of
   (i) a compound of the formula II $$AlR_cO_d \quad (II)$$

wherein

R is an alkyl group having 1 to 20 carbon atoms,
   O is a chlorine atom, a bromine or an iodine atom and
   c and d are 1, 1.5 or 2 and wherein $c+d=3$, and
   (ii) a compound of the formula (III)

$$AlR'_3 \quad (III)$$

wherein R' is an alkyl group having 1 to 20 carbon atoms, wherein the ratio of the compound of formula (I) to the compound of formula (II) is 2 to 10, and
   (C) at least one alcohol,
   at a pressure of 25 kg/cm²G or higher.

2. The process of claim 1, wherein the alcohol is methanol.

3. The process of claim 1, wherein the alcohol is ethanol.

4. The process of claim 1, wherein the alcohol is a mixture of methanol and ethanol.

5. The process of claim 1, wherein the zirconium halide is selected from the group consisting of $ZrCl_4$, $ZrBr_4$, $ZrI_4$, $ZrBrCl_3$ and $ZrBr_2Cl_2$.

6. The process of claim 1, wherein the organoaluminum compound of formula (II) is selected from the group consisting of $Al(C_2H_5)Cl_2$, $Al(C_2H_5)Br_2$, $Al(C_2H_5)I_2$, $Al(CH_3)_{1.5}Cl_{1.5}$, $Al(CH_3)_{1.5}Br_{1.5}$, $Al(C_2H_5)_{1.5}Cl_{1.5}$, $Al(C_2H_5)_{1.5}Br_{1.5}$, $Al(C_2H_5)_{1.5}I_{1.5}$, $Al(C_3H_7)_{1.5}Cl_{1.5}$, $Al(iso-C_3H_7)_{1.5}Cl_{1.5}$, $Al(C_4H_9)_{1.5}Cl_{1.5}$, $Al(iso-C_4H_9)_{1.5}Cl_{1.5}$, $Al(C_8H_{13})_{1.5}Cl_{1.5}$, $Al(C_2H_5)_{1.5}Br_{0.5}Cl$, $Al(C_8H_{17})_{1.5}Cl_{1.5}$, $Al(C_2H_5)(CH_3)_{0.5}Cl_{1.5}$, $Al(C_2H_5)_2Cl$, $Al(C_2H_5)_2Br$, $Al(C_2H_5)_3I$, $Al(CH_3)_3$, $Al(C_2H_5)_3$, $Al(C_3H_7)_3$, $Al(iso-C_3H_7)_3$, $Al(C_4H_9)_3$, $Al(iso-C_4H_9)_3$, $Al(C_5H_{11})_3$, $Al(C_6H_{13})_3$, $Al(C_8H_{17})_3$ and combinations thereof.

7. The process of claim 1, wherein (A) and (B) are in amounts such that Al/Zr is in a molar ration of 1 to 15.

8. The process of claim 6, wherein (A) and (B) are in amounts such that Al/Zr is in a molar ratio of 1 to 15 and the alcohol is selected from the group consisting of methanol, ethanol and propanol.

9. The process of claim 7, wherein the alcohol is in an amount of 0.1 to 6 time sin moles of said zirconium halide.

10. The process of claim 8, wherein the alcohol is methanol in an amount of 0.1 to 5 times in moles of said zirconium halide.

11. The process of claim 8, wherein the alcohol is methanol in an amount of 0.3 to 2.0 times in moles of said zirconium halide.

12. The process of claim 8, wherein the alcohol is ethanol in an amount of 0.1 to 3 times in moles of said zirconium halide.

13. The process of claim 8, wherein the alcohol is ethanol in an amount of 01 to 1 times in moles of said zirconium halide.

14. The process of claim 7, wherein the process is carried out at a temperature of 100° C. to 150° C. and for a reaction time of 15 minutes to 1 hour.

15. The process of claim 13, wherein the zirconium halide is $ZrCl_4$; the alcohol is selected from the group consisting of methanol, ethanol and a mixture thereof, and the organoaluminum compound is a combination of $(C_2H_5)_3Al$ and $(C_2H_5)_3Al_2Cl_3$.

16. The process of claim 1, wherein the linear α-olefin has 6 to 18 carbon atoms.

17. The process of claim 13, wherein the linear α-olefin has 6 to 18 carbon atoms.

* * * * *